US009995684B2

(12) United States Patent
Seidel et al.

(10) Patent No.: US 9,995,684 B2
(45) Date of Patent: Jun. 12, 2018

(54) THERMOPHORESIS MEASUREMENTS IN NANOLITERDROPLETS (71) Applicant: NanoTemper Technologies GmbH, Munich (DE)

(72) Inventors: Susanne Seidel, Munich (DE); Dieter Braun, Lenggries (DE); Stefan Duhr, Munich (DE); Philipp Baaske, Munich (DE)

(73) Assignee: NANOTEMPER TECHNOLOGIES GMBH, Munich (DE)

( * ) Notice: Subject to any disclaimer, the term of this patent is extended or adjusted under 35 U.S.C. 154(b) by 0 days. days.

(21) Appl. No.: 14/533,314

(22) Filed: Nov. 5, 2014

(65) Prior Publication Data
US 2015/0316480 A1 Nov. 5, 2015

(30) Foreign Application Priority Data

May 5, 2014 (EP) .................................... 14167075

(51) Int. Cl.
*G01N 21/64* (2006.01)
*B01L 3/00* (2006.01)
(Continued)

(52) U.S. Cl.
CPC ........ *G01N 21/6486* (2013.01); *B01L 3/5027* (2013.01); *B01L 3/50851* (2013.01);
(Continued)

(58) Field of Classification Search
CPC ........... G01N 21/6486; G01N 15/0205; G01N 21/645; G01N 21/6456
See application file for complete search history.

(56) References Cited

U.S. PATENT DOCUMENTS

2010/0044586 A1* 2/2010 Duhr ................ B01L 3/502761
250/459.1
2010/0330578 A1* 12/2010 Duhr ................ G01N 21/6408
435/6.11
(Continued)

OTHER PUBLICATIONS

Bransky et al., A microfluidic droplet generator based on a piezo-electric actuator, Nov. 20, 2008, Royal Society of Chemistry, vol. 9, pp. 516-520.*
(Continued)

*Primary Examiner* — Christine S Kim
(74) *Attorney, Agent, or Firm* — Westman, Champlin & Koehler, P.A.

(57) ABSTRACT

The present invention relates generally to a system and a method for thermo-optical measurements in a droplet of aqueous solution comprising particles of interest, the method comprising the following steps: providing the droplet of aqueous solution with a volume of less than 200 nl, wherein the aqueous solution is a first liquid and at least a part of the particles of interest are fluorescent particles; embedding the droplet of aqueous solution at least partly in a second liquid; irradiating a laser light beam into the droplet to obtain a spatial temperature distribution in the droplet around the irradiated laser light beam; exciting fluorescently said fluorescent particles and detecting fluorescence at least at one position or at around one position in the droplet or detecting the fluorescence distribution of said fluorescently excited particles, wherein said detection of fluorescence is performed at least once at a predetermined time after the start of the laser irradiation; and determining a characteristic of the particles of interest from the detected fluorescence intensity or fluorescence intensity distribution.

20 Claims, 5 Drawing Sheets (51) Int. Cl.
*G01N 15/02* (2006.01)
*B01L 3/02* (2006.01)

(52) U.S. Cl.
CPC ....... *G01N 15/0205* (2013.01); *G01N 21/645* (2013.01); *G01N 21/6456* (2013.01); *B01L 3/0268* (2013.01); *B01L 2200/0642* (2013.01); *B01L 2200/0673* (2013.01); *B01L 2300/0663* (2013.01); *B01L 2300/0819* (2013.01); *B01L 2300/0829* (2013.01); *B01L 2300/0838* (2013.01); *B01L 2300/1872* (2013.01); *B01L 2400/0451* (2013.01); *G01N 2201/06113* (2013.01)

(56) References Cited

U.S. PATENT DOCUMENTS

2011/0084218 A1* 4/2011 Duhr ................. B01L 3/508
                                                     250/459.1
2015/0332499 A1* 11/2015 Schuldt ............... G06T 17/00
                                                     345/426

OTHER PUBLICATIONS

Ellson et al., Transfer of Low Nanoliter Volumes between Microplates Using Focused Acoustics—Automation Considerations, JALA, Oct. 1, 2003, pp. 29-34.*

Lee, Chuang-Yuan et al., "Microreactions Using Nanoliter Droplets With Oil Encapsulation", 2007, Kobe, Japan, Jan. 21-25, 2007, 1-4244-0951-9/07/$25.00©2007 IEEE, 4 pages.

Labcyte: "Acoustic Droplet Ejection", Feb. 28, 2008, p. 70090986, XP055144871, retrieved from the Internet: URL: http://www.nanodaten.de/uploads/data_sheets/90f2974b9078d7c976415875660c5lel.pdf (retrieved by the EPO on Oct. 7, 2014), 2 pages.

Bransky, Avishay et al., "A microfluidic droplet generator based on a piezoelectric actuator", ©The Royal Society of Chemistry 2009, Lab Chip, 2009, 9, 516-520, 6 pages.

Baaske, P. et al., "Some like it hot: immobilization-free, contact-free molecular interaction studies using microscale thermophoresis", http://registration.akm.ch/einsicht.php?XNABSTRACT_ID=924 . . . , MipTec 2009—The Leading European Even for Drug Discovery, Oct. 14, 2009, 1 page.

Ellson, R. et al., "Transfer of low nanoliter volumes between microplates using focused acoustics?automation considerations", Journal of the Association for Laboratory Automation, vol. 8, No. 5, Oct. 1, 2003, pp. 29-34, XP055145032, ISSN: 1535-5535, DOI: 10.1016/51535-5535(03)00011-X; Abstract Only.

Extended European Search Report for European Patent Application No. 14167075.2, dated Oct. 17, 2014, 10 pages.

* cited by examiner

THERMOPHORESIS MEASUREMENTS IN NANOLITERDROPLETS

CROSS-REFERENCE TO RELATED APPLICATION

This Application is a non-provisional Application of European Patent Application No. 14 16 7075.2, filed 5 May 2014, in German, the contents of which are hereby incorporated by reference in their entirety.

In the last years, thermophoresis, the directed movement of molecules along a temperature gradient, has successfully been utilized to quantify biomolecule interaction in different fields of life sciences. The present invention relates generally to a new system and a method for generating nano liter volumes from a first liquid sample at least partially embedded in a second liquid and to perform thermo-optical measurements in such small volumes of the first liquid.

In particular, the present invention relates to a method and a system to measure characteristics of biomolecules, the interaction of biomolecules with, e.g. modified biomolecules/nanoparticles/microbeads and/or the determination of the length/size (e.g. hydrodynamic radius) individual biomolecules/nanoparticles/microbeads and/or the determination of length, size (e.g. hydrodynamic radius) in all possible combinations of two or more. It is of note that the present invention is, however, not limited the measurement/characterization of biomolecules. Therefore, also the characteristics of other compounds/particles can be measured and determined by the means and methods disclosed herein, for example kinetic events and interactions of molecules may be determined and/or measured. Accordingly, also chemical reactions (like inorganic or organic reactions) may be measured by the methods and under use of the devices of the present invention. It is also envisaged to determine complex formations and/or their dissociation.

BACKGROUND OF THE INVENTION

Molecular recognition is not only central to signal transduction in living systems, but also represents the functional principle of pharmaceuticals and laboratory diagnostics. A variety of opportunities thus comes along with an in-depth understanding of biological binding events. From this perspective, it is not surprising to see an ever-growing interest in quantitative biomolecule interaction analysis. To this end, the directed movement of molecules along a temperature gradient, referred to as thermophoresis, has successfully been utilized in the last years. Thermophoresis measurements are highly sensitive to molecular size, charge, and/or conformation. At least one of these parameters is measurably influenced upon each biomolecular interaction. Based on this influence, affinity and/or concentration can be quantified, even in complex bioliquids.

In the well established microscale thermophoresis (MST) approach, which has successfully been commercialized by NanoTemper Technologies GmbH, samples are measured in glass capillaries. Capillary MST has been applied, for example, for ions, small molecules, nucleic acids, peptides, proteins, crude cell lysate, and untreated human blood serum. With about 0.5 µl per capillary filling, i.e., 0.5 µl handling volume, the sample consumption is low compared to, e.g., isothermal titration calorimetry.

It is also known that thermophoresis measurements can be carried out in small droplets with a volume in the range of µl. Such droplets could be produced by using micropipettes. It was also known to cover such µl droplets with oil to prevent evaporation.

The additionally consumed volume becomes essential when working with expensive or rare material, like patient samples. This is especially true if high-throughput analyses need to be performed, e.g., in diagnostics or drug discovery. Throughput and automation of conventional MST might be limited by the handling of glass capillaries.

The inventors of the present invention noted that there is a need for an improved technique for thermophoresis measurements. It is further noted that there is a need for a more efficient and/or more effective and/or faster technique for thermophoresis measurements.

Therefore, the present invention provides for an improved system and method for thermophoresis measurements in very small volumes, preferably very small droplets.

The objects of the invention are achieved by the features of the independent claims. Further preferred embodiments are characterized in the dependent claims.

SUMMARY OF THE INVENTION

The technique of the present invention allows for thermo-optical measurements, preferably thermophoresis measurements, in very small volumes, preferably volumes of less than 500 nl, more preferably less than about 200 nl. In particular, the handling volume or working volume of a sample liquid which is needed to perform optical measurements is preferably less than 200 nl.

According to the present invention, the handling or working volume of less than 200 nl is preferably provided as a first volume of an aqueous solution, which is a first liquid, wherein the boarder of the first volume is formed with regard to a second liquid. According to the present invention it is preferably that the first liquid and second liquid are immiscible. In other words, it is preferred that the first liquid forms a first phase and the second liquid forms a second phase. In the following, the first liquid is also called sample liquid or sample fluid whereas the second liquid is also called carrier liquid or carrier fluid.

According to a first preferred embodiment, the present invention relates to a method for thermo-optical measurements in a very small first volume in form of a droplet, i.e., the small handling/working volume is provided in form of a droplet. The droplet is preferably formed from an aqueous solution which comprises particles of interest, i.e., particles which should be characterized by means of the thermo-optical measurements. The method comprises at least one of the following steps.

The droplet is provided with a volume of preferably less than 200 nl. Preferably, the droplet comprises a first liquid with an aqueous solution or is a first liquid in form of an aqueous solution. Said first liquid comprises the particles of interest. Some of the particles of interest are fluorescent particles. In particular, it is known that bio molecules, e.g., proteins, peptide or small molecules in cells are naturally fluorescent, which is called intrinsic fluorescence or autofluorescence (such as NADH, tryptophan, tyrosine, phenylalanine or endogenous Chlorophyll, Phycoerythrin or green fluorescent protein). Additionally or alternatively, the particles of interest can be "labelled" or "marked" fluorescently. In particular, the particles of interest can be "labelled" or "marked" with an extrinsic fluorophore, a fluorescent dye which can be a small molecule, protein or quantum dot. Several techniques exist to exploit additional properties of fluorophores are known in the art. The droplet with the aqueous solution, i.e., the first liquid is embedded at least partly in a second liquid. Then, a laser light beam is irradiated into the droplet to obtain a spatial temperature distribution in the droplet around the irradiated laser light beam. According to a first embodiment, the laser light beam creates a change of temperature within the whole first volume, e.g., the temperature in the entire droplet is raised. Still in other words, the entire liquid of the handling volume or working volume is heated by the laser beam. According to a further preferred embodiment, however, only the area around the laser beam inside the droplet is heated, whereas areas inside the working volume (droplet) which are sufficiently far spaced away from the laser beam are not heated (quasi not heated). For instance, in case the droplet is large enough and the focusing of the laser beam is very sharp, it is possible to substantially heat only a small area inside the droplet. In this case, the measurement volume is even smaller than the handling volume.

The fluorescent particles are fluorescently excited such that the fluorescence is detected at least at one position or at around one position in the droplet. Moreover, a fluorescence distribution of said fluorescently excited particles, an absolute value and/or a time dependency of the fluorescence is detected and preferably performed at least once at a predetermined time after the start of the laser irradiation. Finally, a characteristic of the particles is determined based on the detected fluorescence intensity and/or fluorescence intensity distribution.

According to a first preferred embodiment, the droplet is fully embedded within the second liquid. The laser light for fluorescently exciting the fluorescent particles is preferably infrared (IR) light. Accordingly, it is preferred that the second liquid does preferably not absorb IR radiation, or at least does not reduce the intensity of the IR light more than 50%.

According to a further preferred embodiment, the second liquid covers a large part of the surface of the droplet, preferably more than 80%, more than 90% or even more than 95% of the surface of the droplet with a layer of the second liquid. For instance, in case a droplet touches or adheres to a surface of solid matter, said touching/adhering contact of the droplet is then preferably not covered by the second liquid.

Irrespectively, whether the droplet is fully or only partly covered by the second liquid, it is preferred that the aqueous solution of the first liquid does not dissolve with the second liquid such that a boundary surface is formed between the aqueous solution (first liquid) and the second liquid.

For instance, the second liquid (carrier fluid) is preferably non-aqueous, an oil, a surfactant, a surfactant-oil mix or a detergent-oil mix. For instance, the second liquid may comprise or may be formed from fluorocarbon, preferably non porous fluorocarbon, which provides the further preferred advantage of small autofluoreszence. Moreover, water-in-oil emulsion drops are preferably formed and stabilized with phospholipids which can adhere and form a bilayer. This preferably ensures that the aqueous solution of the first liquid is a bordered, delimited or well defined volume which preferably forms a droplet, preferably a spherical droplet. Depending on the properties of the two liquids, however, it is also possible that the delimited volume forms an oval or egg shaped droplet, an elongated volume, a partly flat volume, partly convex or partly concave droplet, which comprises preferably a substantially stable diameter.

The present invention is not limited to any particular technique to form the small droplets with a volume of preferable less than 200 nl. For instance, a droplet may be formed by the following steps: providing a destination plate with the second liquid; providing a liquid sample of the aqueous solution containing said fluorescent particles and generating at least one transfer droplet from said liquid sample; and transferring at least one transfer droplet to the second liquid such that a droplet is formed by one or a plurality of said transfer droplets on the destination plate, wherein said droplet is at least partly embedded in said second liquid.

According to a preferred embodiment of the present invention, the destination plate is a multiwell plate (often also called microtiter plate or mircroplate) and the second liquid is preferably provided in at least one of the wells of the multiwell plate. The thickness of the second liquid is preferably below 500 μm, preferably below 250 μm. Preferably, the destination multiwell plate comprises conical wells and the droplet preferably touches a bottom of the conical well. It is further preferred that the droplet is substantially spherical even when the droplet touches or adheres to the bottom of a destination plate.

The liquid sample is preferably provided in a multiwell source plate.

The transfer droplets are preferably generated by a droplet generator. Such a droplet generator may comprise a transducer which is preferably located below the (multiwell) source plate, wherein the transducer preferably which emits pulses, preferably acoustic pulses, to generate and transfer a droplet from the (multiwall) source plate to the destination plate.

Moreover, droplets, preferably monodisperse droplets can be generated in microfluidic devices. For instance, it has been shown in the past that droplets of microfluidic origin are suitable for quantitative assays. Moreover, it is also known to injected droplets, preferably droplets, which are embedded in a second fluid, into a sorting device, and a guiding through a branch of channels is possible by means of an electric field.

Moreover, a variety of different flow-focusing junctions are known with varying nozzle sizes and numbers of inlets are known for a droplet generation.

Thus, the droplets of the present invention can also be produced with a microfluidic system for sequential sampling of droplets. Such a system comprises, for instance, at least one reservoir containing a sample fluid (e.g. the first liquid) and a carrier fluid (e.g. the second liquid); one or more droplet generators, each comprising an opening, or 'microsampling tip', for the controlled sampling of droplets from a sample reservoir; and channels or tubing or capillary to conduct the droplets in the carrier fluid, and optionally a source of pressure. The means for generating small droplets may further comprise a microfluidic chip supporting channels or capillaries to conduct one or more droplets in a carrier fluid. The tubing or capillary may connect the microsampling tip with the microfluidic chip.

Microfluidic chips are known in the art. For instance, such microfluidic chips may be made of glass or polymer and fabricated using standard microfabrication techniques.

Preferably, a droplet generator can be electronically controlled and can accordingly comprise an electronically driven microsampling head, which preferably comprises an opening, or 'microsampling tip', for generating droplets of fluid.

Preferred advantages of such a droplet generator may be briefly summarized as follows: droplet size can be accurately pre-determined; droplets can be generated at high speed (for example, 1 Hz-1 kHz, for example, 1 Hz-100 Hz);

only very small sample volumes are required to generate large numbers of sample droplets; droplets of different sizes can be created, and preferably droplet size can be controlled for each individual droplet; spacing between the droplets can be accurately controlled.

Accordingly, such droplet generators provide the preferred be of high-throughput, in terms of sample volume needed, number of samples that can be run per day, and cost. In conventional microfluidic systems, a larger amount of sample volume is required, and only a few samples per day can be measured. According to a further embodiment, the second liquid is mixed with the aqueous solution such that droplets of the aqueous solution are formed within the second liquid. These droplets are preferably fully embedded within the second liquid.

The second liquid with said droplets may be guided into a channel or capillary. Thus, in case the diameter of the droplet is larger than the diameter of the channel, or the diameter of the droplet substantially corresponds to the inner diameter of the channel, the droplets may touch the channel at the inner surface of the channel, such that at least a large part of the surface of the droplet is still covered by the second liquid. Such channel can be provides as channel of a microfluidic device.

Accordingly, it is also possible to guide the second liquid with a plurality of droplets of the first liquid through a capillary or channel/tubing, e.g., the tubing of a microfluidic device, such that a "train of droplets" is provided. Depending on the size of the volume of the individual droplets in comparison to the tubing, the droplets can be provided fully embedded within the second liquid or only partly embedded, e.g., the droplet is in contact to the inner surface of the tubing. Moreover, in case the tubing is very small compared to the inner diameter, also cylindrically shaped droplets may be formed inside such tubing. Such droplets can be separated from neighbouring droplets by means of the second liquid. Moreover, the shape of the first fluid volume (droplet) is not only dependent on the exterior shape of the tubing but also on the hydrodynamics of the fluid, particularly in relation to the geometry of the tubing.

According to a further preferred embodiment it is possible to provide the laser (e.g. IR laser) and preferably also the means for fluorescently exciting fluorescent particles stationary with regard to such a tubing/capillary, whereas the droplets are guided through the tubing/capillary. Such an arrangement provides the further preferred advantage that measurements can be performed parallel. For example, a plurality of tubes are provided parallel and the laser for heating the droplet is provided in form of a line shaped laser. The thermophoretically induced movement of particles inside the heated droplets can be monitored by means of a CCD/CMOS camera or an array of diodes.

Still in other words, the droplets of the first liquid are provided in the second liquid as an emulsion. The development of microfluidics offers new opportunities to investigate emulsion features and behaviours.

As mentioned above, the present invention is not limited to a particular method for generating the small droplets. For instance, a droplet can also be generated by means of a piezo based droplet generator.

According to the present invention it is preferred to produce very small droplets, wherein the volume of the droplet is preferably smaller than 100 nl, preferably smaller than 50 nl, preferably smaller than 10 nl, preferably smaller than 5 nl, preferably smaller than 2 nl, preferably smaller than nil, preferably smaller than 500 pl, preferably smaller than 200 pl.

On the other hand, it is further preferred that the volume of the droplets is larger than 10 pl, preferably larger than 50 pl, preferably larger than 100 pl.

Moreover, it is further preferred that the diameter of the droplet is smaller than 200 µm, preferably smaller than 115 µm and/or preferably larger than 500 nm.

The fluorescence is preferably detected at least at two positions or at around two positions in droplet. The additional detection of fluorescence is preferably performed at least once before the start of the laser irradiation.

As mentioned above, it is preferred that the laser is a IR laser and/or the fluorescence is excited with a light emitting diode, LED or with a laser. For instance, depending on the size of the droplet, exciting with an IR laser can be a further preferred advantage, since laser light could be easily focussed inside a small droplet. Light from LEDs can typically be focused to a spot of 100 µm diameter or larger. This would mean light of LEDs would illuminate the entire droplet. Laser light can be focused to an even smaller spot size, e.g. down to 1 µm diameter. This allows illumination of only part of a droplet. This may allow obtaining information on local concentration/fluorescence distribution. This may be advantageous for thermo-optical measurements.

According to a further preferred embodiment it is preferred to use a low power IR laser within the range of from 5 mW to 60 mW.

According to a further aspect, the present invention also relates to a method for generating droplets from a liquid sample, wherein the method comprises the steps of: providing a destination plate; providing a liquid sample and generating droplets from said liquid sample and transferring said droplet to the destination plate such that a droplet is formed by one or a plurality of said droplets on the destination plate.

Preferably, a preformed protection film is provided on the destination plate such that the droplets are transferred in said protection film on the destination plate.

According to a further preferred embodiment, the protection film may be formed on the destination plate subsequently, e.g., after the droplets are formed on the destination plate.

The thermophoresis characterization, which is a preferred embodiment of the thermo-optical measurement, allows to determine properties of particles in aqueous solutions. It also allows to discriminate between different conformations of one species of particle and it also allows to discriminate between different species of particles. The characterization can be used in all cases where the particles show a response to changes in the temperature gradient and changes in the absolute temperature. A preferred key feature of thermophoresis is, that a defined spatial temperature distribution is generated locally on microscopic length scales. Another preferred key feature is, that the response of the particles is assigned to a certain place of the known, optically generated spatial temperature distribution. Thereby, temperature, place and response of the particles are directly correlated.

Thermophoresis characterization is based on the creation of strong temperature gradients at microscopic length scales in aqueous solution. By doing so, the energetic states of the molecules dissolved in the solution are changed depending on the temperature and the properties of the molecule. To put it in other words, the molecules experience a spatial potential originating from the spatial differences in temperature. This potential drives a directed motion of molecules along the temperature gradient, an effect called thermophoresis. In other cases the change in temperature leads, beside thermophoresis, to an unfolding of biopolymers like proteins or DNA. The unfolding effect is observed at high temperatures and is a measure for the stability of molecules (The reason for unfolding is the increased influence of the entropy component of the energy). The effect is separated from thermophoresis by a characteristic time scale. The stability analysis takes place in milliseconds to one second, while thermophoresis is observed at times in a range from 1 second to 50 seconds, preferably 1 second to 40 seconds.

Thermophoresis is a method which is sensible to surface properties of molecules in a solution. It is not necessary to expose molecules to a different matrix (like in chromatography) or to interact with the molecules physically in any way (e.g. by direct contact or by adding substances). Only interactions between electromagnetic waves and matter are necessary. Infrared radiation is used for spatial heating (i.e. manipulation of matter) and fluorescence to detect molecules.

The gist of thermo-optical characterization based on thermophoresis is that differences in thermophoretic mobility (e.g. the velocity of molecules in a temperature gradient), and hydrodynamic radius can be detected by analyzing the spatial distribution of concentration (i.e. fluorescence) or the fluctuations of single particles trapped in the spatial temperature profile. While the hydrodynamic radius is only related to the radius of a molecule, the thermophoretic mobility is sensitive to charge, surface properties (e.g. chemical groups on surface), shape of a molecule (i.e. size of surface), conformation of a protein or interaction between biomolecules or biomolecules and particles/nanocrystals/microbeads. This means that if any of the mentioned properties are changed the molecules will experience a different thermodynamical potential, resulting in differences in thermophoretic mobility (i.e. change in spatial concentration profile or fluctuation amplitude of trapped particles).

Thus, the present invention generally relates to thermally induced processes, e.g. temperature gradient induced directed motion or thermal denaturation.

The present invention is not limited to any particular type of molecules. Accordingly, in the context of this invention, in particular the claims, it is noted that the terms "particle" or "particles" preferably relates to the nucleic acids (such as DNA, RNA, LNA, PNA) to be analyzed by the means, methods and devices of the present invention. Moreover, the term "particle", "modified particle", "modified bead" or "modified nucleic acid molecule" relates in particular to beads/particles/nucleic acid molecules which comprise or are linked to other molecules, like other bio molecules (like peptides, proteins amino acids etc) or labels, like fluorescent labels. This also comprises coating of such beads or particles with these nucleic acid molecules to be analyzed or measured and determined in accordance with this invention.

Accordingly, the thermo-optical characterization of the present invention provides the means for fast all optical biomolecule analysis. In this context, particles of interest which are fluorescently or labelled are also called modified biomolecules, nanoparticles, or microbeads which comprise fluorescently labelled biomolecules, nanoparticles, or microbeads. Fluorescently labelled biomolecules, nanoparticles, or microbeads may be e.g. biomolecules, nanoparticles, or microbeads, to which one or more fluorescent dyes have been attached, e.g. covalently attached. Moreover, the terms "marked" and "labelled" are used synonymously in the context of this invention.

In contrast to the above discussed well known techniques, the handling or working volume according to the present invention is significantly smaller: it lies in the range of several nl or even below.

In particular, the present invention relates to a novel technique which allows for thermophoresis measurements in very small volumes, e.g., total volumes down to 10 nl or even smaller. Instead of capillaries, measurements are preferably performed in droplets. In the following the sample droplets which will be used for the measurement will also be called droplets, since droplets within a range from 2-10 nl are preferred. The term droplets as used in the present disclosure, however, does not restrict the volume to a particular range of nl but also refers to droplets with less volume, e.g., sub-nl droplets with a volume of several pl.

The droplets may be formed by a single droplet. According to other embodiments, however, a plurality of droplets could be combined to form a droplet.

Figure 1:
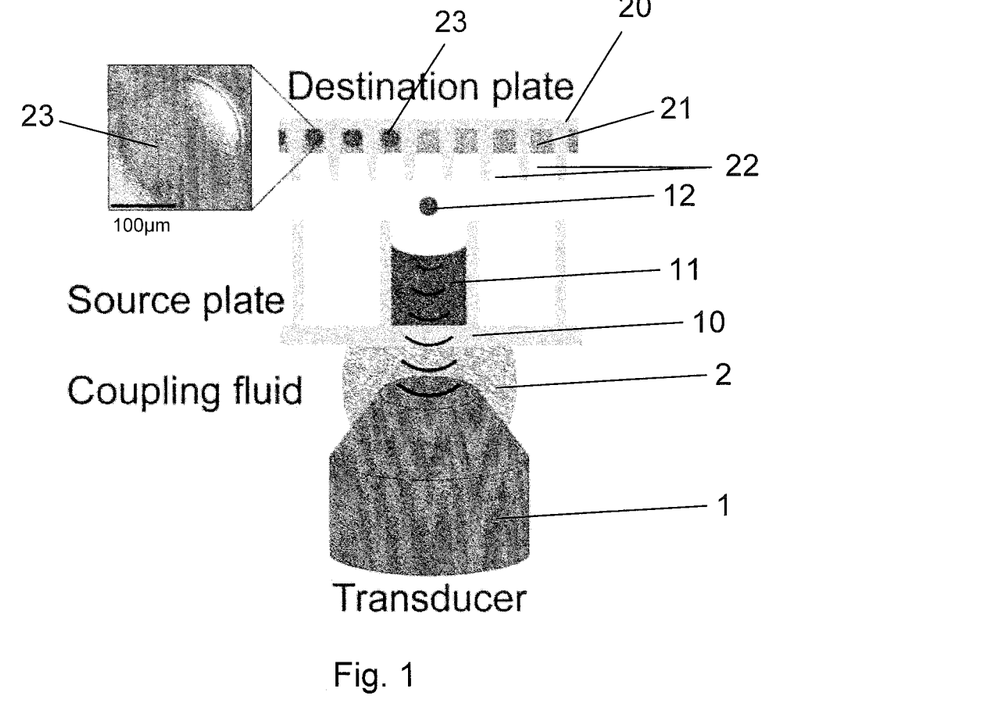
FIG. 1 shows a schematic example for a droplet sample production according to the present invention.

Droplets are preferably produced using a commercially available, non-contact acoustic liquid handling system (see FIG. 1; Echo® 550 Liquid Handler, Labcyte Inc., USA). Other sample preparation methods, e.g. via microfluidic devices, could also be used and might allow to further reduce the sample volume down to pico liter (pl). For instance, ink jet printers can produce droplets with a volume down to 100 pl. Accordingly, microfluidic devices which work by the same principles as ink jet printers can be used in the present invention.

To protect the droplets from evaporation they are preferably covered by a protective cover layer, preferably an oil layer. According to a first preferred embodiment, droplets are transferred into a (protective) oil layer, to form droplets which are covered by said oil layer. Alternatively, droplets can be transferred to a destination plate to form droplets, wherein these droplets are subsequently covered with an oil film. Common to both preferred techniques is the cover layer, e.g., the oil film which reduces or prevents evaporation of the sample of the droplets.

Further stabilization of the droplets, which are preferably aqueous droplets, under the cover layer is preferably achieved by using a special surfactant blend. With the method of the present invention, it is possible to reproducibly obtained droplets which are stable for several hours.

Thus, according to the present invention it is possible to significantly reduce the actual handling/working volume, e.g., it is preferably smaller than 500 nl, preferably smaller than 200 nl, preferably smaller than 100 nl, preferably smaller than 50 nl, preferably smaller than 10 nl, preferably smaller than 5 nl, preferably smaller than 2 nl, preferably smaller than 1 nl, preferably smaller than 500 pl, preferably smaller than 200 pl, preferably smaller than 100 pl. The volume of the first volume is preferably larger than 10 pl, preferably larger than 50 pl, preferably larger than 100 pl. Moreover, it is further preferred that the diameter of a droplet is smaller than 200 µm, preferably smaller than 115 µm and/or preferably larger than 500 nm.

Since the amount of sample volume becomes essential when working with expensive or rare material as for instance patient samples, the present invention provides several advantages over the known prior art methods. This is especially true if high throughput analyses need to be performed, e.g. in molecular diagnostics or drug screening.

For instance, compared to the conventional capillary-based approach, the novel technique of the present invention leads to a significant sample reduction and is automation friendly. When the samples are measured in droplets under oil, preferably surfactant stabilized, the technique can also provide a solution to the often observed problem of unspecific surface adsorption of biomolecules to the glass capillary walls. The approach of the present invention is high throughput and automation friendly, not only due to volume reduction, but also because it can be used in combination with conventional microwell plates. Microwells are standardized sample containers which are easy to handle and well suited for implementation into existing automation platforms. An additional benefit of the present invention is the fact that the biomolecule solutions do preferably not get in contact with plastic or glass surfaces. This obviates the risk of unspecific surface absorption ("sticking") of the biomolecules, an often observed obstacle e.g. in capillary thermophoresis. In addition, aspects of the present technology allow reduction of dead volume of the measured samples and thus improve efficiency.

The droplet measurements according to the present invention are preferably performed on a newly constructed setup. As in the capillary based format, thermophoresis is preferably measured all-optically, i.e., the temperature gradient is preferably induced optically, e.g., via laser heating, preferably infrared laser heating. Also the effect of the generated temperature gradient is preferably detected optically, e.g., recorded via fluorescence of at least one of the biomolecules in the sample.

However, some alterations compared to the instrument for capillary measurements are preferably implemented. According to a preferred embodiment, an inverted configuration is used. In particular, it is preferred that the plate containing the samples (droplets) should not stay upside down during measurement to avoid dripping.

In addition, sequential measurement of multiple samples is preferably no longer be realized by a linear movement of the tray carrying the samples (droplets) as preferred in the capillary setup. It is preferred that the sample well plate is fixed, which has the potential advantage to guarantee that the samples/droplets substantially stay in their position inside the well during measurements. Accordingly, it is preferred that the optical parts of the setup, e.g. which comprise IR-laser, LED and/or CCD-camera, are preferably mounted onto a translation stage or onto a plurality of translation stages to allow for movements, e.g. in x, y and/or z direction. In particular, fluorescence excitation can preferably be achieved by an LED or by a laser. Preferred is a light source which emits light at a wavelength between 260 nm and 800 nm. According to further preferred embodiments, the fluorescent light can be detected by a photodiode, as CMOS camera, generally known image sensors, a photodiode array, an APD (Avalanche Photo Diode), a PMT (Photo Multiplier Tube), and/or MPPCs (Multi Pixel Photon Counters).

This allows that droplets could be assessed sequentially, even when the well plate is kept stationary.

Using the new approach according to the present invention, it is possible to characterize thermophoresis and also other temperature induced effects in droplets. The approach of the present invention was already successfully applied for the binding quantification of a specific DNA-aptamer to its target, the small molecule AMP which will be discussed in further detail below.

The technique of the present invention will have a comparably wide range of application possibilities as capillary based thermophoresis, including label free protein measurements and assays in complex bioliquids e.g. in serum for diagnostics.

BRIEF DESCRIPTION OF THE DRAWINGS

In the following, preferred embodiments of the present invention are described in detail with reference to the Figures.

DETAILED DESCRIPTION OF THE DRAWINGS

The system and method of the present invention generally relates to a capillary-free approach to measure thermophoresis in droplets, preferably under a protection layer. The protection layer is preferably an oil layer, further preferred an oil-surfactant layer (see FIGS. 1 and 2). The sample droplets, i.e., the droplets which are formed for the measurement are droplets, which may be formed from a plurality of produced droplets. Preferably, the sample droplets/droplets are based on an aqueous solution. Such a water-in-oil system is characterized for temperature induced effects in experiment and agreed with numerical simulations.

The system's applicability for biomolecule interaction studies was evaluated with a well described nucleic acid aptamer. Aptamers have been discovered more than 20 years ago. Owing to their three-dimensional conformation, these single stranded oligonucleotides bind to various biomedically relevant targets including proteins and small molecules. Just like antibodies, aptamers show high specificity and affinity. At the same time, these nucleic acid based ligands are superior to protein based ones in production costs, storage conditions, and chemical modifiability. In vivo, their small size facilitates good delivery to the target tissue whereas no immunogenicity and low toxicity have been reported. These benefits and the first marketed aptamer drug demonstrate the high potential of aptamers.

Aptamer binding was studied by using the method of the present invention. In particular, a non-contact liquid handling system available commercially (e.g. Labcyte) was used to generate the sample droplets. The used system preferably delivers 2.5 nl-portions from multi-well source plates into destination plates via acoustic droplet ejection (see FIG. 1). The transfer volume accuracy is preferably <2%. To prevent evaporation, droplets were preferably transferred into a protective layer of standard microbiology mineral oil, preferably supplemented with a surfactant mix as disclosed in S. Tawfik, A. D. Griffiths, *Nat. Biotechnol.* 1998, 16, 652-656.

FIG. 1 shows a preferred embodiment for a droplet sample preparation according to the present invention. A well of a source well plate 10 is filled with a liquid sample 11 (purple). A destination plate 20 with a plurality of wells 22 is located above the source well plate 10. The wells 22 of the destination plate 20 are filled with an oil 21, preferably a surfactant-oil mix 21 (brown). In the droplet generator, preferably an Echo® 550 Liquid Handler (Labcyte Inc.), a transducer 1 emits a pulse, preferably an acoustic pulse, which is preferably transferred through a coupling fluid 2 into the source well 10 and leads to the formation of a defined droplet, e.g., a 2.5 nl droplet 12. The inset of FIG. 1 shows a photo of a 5 droplet 23 (scale bar 100 pm) from a production which was optimized to yield nl-samples stable for several hours. The sample is preferably prepared with the following method steps:

The liquid handler positions a destination plate 20 preferably upside down above a source plate 10 containing a sample stock 11 (purple). The transducer 1 emits an acoustic pulse focused to the sample surface, whereby a 2.5 nl droplet 12 is formed and travels, preferably upward, into the destination well 22 of the destination plate 20. Afterward, transducer 1 and/or destination plate 20 move to the next well. The source plate 10 is preferably maintained stationary. To prevent evaporation, the droplets 12 are transferred into a second liquid 21, preferably an oil-surfactant mix 21 (brown). Produced droplets/sample droplets 23 were stable for several hours as assessed with an inverted light microscope. The thickness of the layer of the second liquid 21 is preferably 1 mm or even smaller. As mentioned above, the delimited volume of the first liquid does not necessarily form a droplet. Depending on the individual properties, it is also possible that the first liquid forms a layer covered by the second liquid. For instance, in accordance with the present invention it is possible to measure in a layer formed from the first liquid, wherein said layer has a thickness of 200 µm or less.

Figure 2:
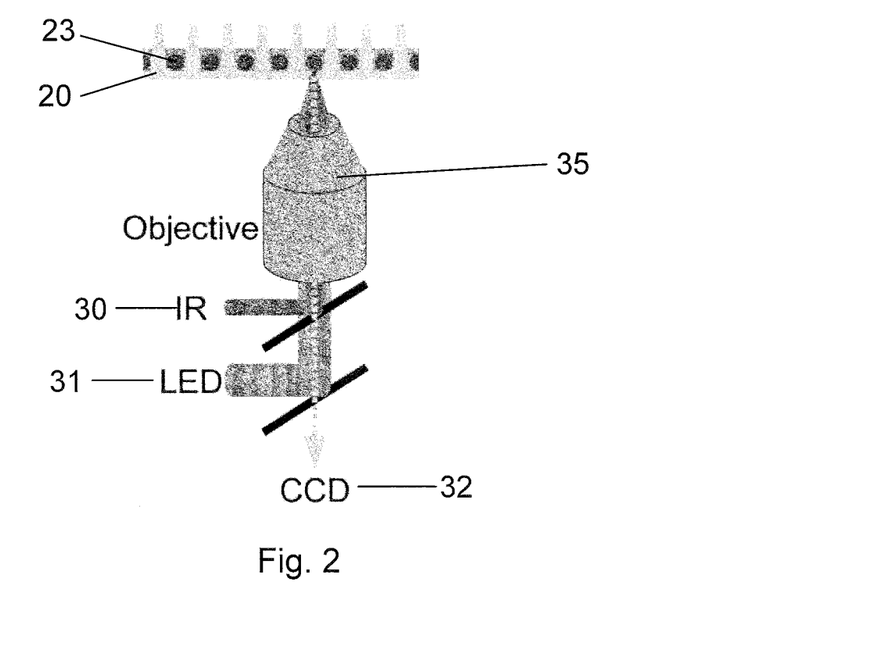
FIG. 2 shows a schematic well plate based thermophoresis measurement in an droplet according to the present invention.

After creation of the droplets 23, these droplets were measured on a newly constructed microscopic setup (see FIG. 2). Similar to the above mentioned capillary instrument, thermophoresis was induced and analyzed all-optically. As an essential modification to the capillary setup, however, it was preferred to use an inverted configuration so that the sample plate 20 (destination plate) stayed upright to avoid oil dripping. It is further preferred to fix the plate 20 which guarantees that the droplets 23 stay in place. In this configuration it is preferred to move (only) the optical parts which allows sequential measurements.

An infrared (IR) laser 30 is focused into the center of the droplet 23, preferably with a 20× objective 35. Laser absorption by the droplet's water molecules leads to local heating. The resultant thermophoretic molecule depletion in the heat spot is preferably monitored via fluorescence, which is excited with a light emitting diode (LED) 31 and recorded with a charge-coupled device (CCD) camera 32. Mounting the optical parts onto a common or a plurality of translation stages allows movements in all three directions (x, y, z) and thus the sequential analysis of multiple sample droplets.

According to a preferred embodiment, four or eight or more droplets, e.g., 2.5 nl portions/droplets are transported to yield 10 nl-(270 µm) or 20 nl-samples (340 µm). Individual portions often do not meet as deflection by the oil reduced the transfer's positional accuracy. To induce coalescence, it is preferred to use destination plates 20 with funnel-shaped wells 22 which are preferably mildly centrifuged after transfer (≤5500×g to avoid droplet damage). With the method according to the present invention, it is possible to reproducibly obtain nl-samples stable for several hours. This allows for multiple thermophoretic binding assays (e.g. 10 min each).

Figure 3:
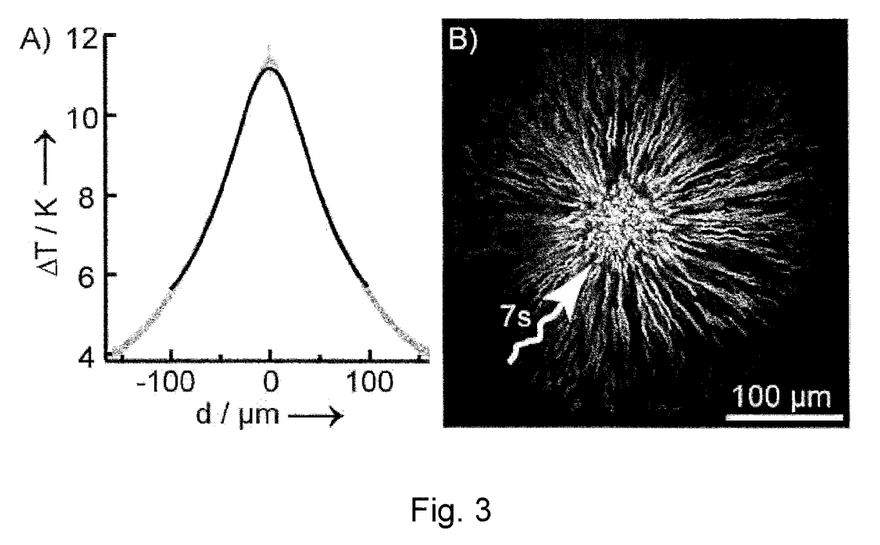
FIG. 3 illustrates the effect of a local heating of 20 droplets, wherein FIG. 3 A) shows a radial temperature profile in a central horizontal plane and FIG. 3 B) is integrated over 7 s of heating.

Before studying biomolecule affinity, the effects of local heating on aqueous droplets under oil was examined. For instance, when asymmetrically applied, heating may occasionally lead to convective flows strong enough to move an entire droplet away from the laser spot. This is preferably prevented by using plates with a comparatively small well floor area (e.g. r=0.45 mm). Utilizing the temperature dependence of the fluorescent dye, e.g., Alexa 647, the radial temperature profile in a 20 droplet's central horizontal plane was obtained 0.2 s after the IR laser had been turned on (FIG. 3). For a temperature increase of $\Delta T_c=11$ K in the heat spot center, the droplet's periphery warmed up by $\Delta T_p=4$ K. A Lorentz fit revealed an FWHM of 120 µm. In the following, $\Delta T$ is defined as the average temperature increase of the central (30×30) µm area.

FIG. 3 shows the local heating of 20 droplets. In particular, FIG. 3 A) shows a radial temperature profile in the central horizontal plane (red). The temperature increased by $\Delta T_c=11$ K in the heat spot center and by $\Delta T_p=4$ K in the droplet's periphery. A Lorentz fit (black) revealed an FWHM of 120 µm.

FIG. 3 B) shows a flow profile of fluorescent polystyrene beads (d=1.0 µm) integrated over 7 s. 100 frames during laser heating were superposed and the averaged background was subtracted. The beads moved toward the heat spot and out of focus with a peak velocities of 5-10 µm/s for $\Delta T=6$ K and 15 µm/s for $\Delta T=15$ K. To elucidate these flows, full numerical simulations considering diffusion, convection, thermophoresis, and the temperature dependence of the dye was performed. Simulations of 20 nl (FIG. 4) and 10 droplets (FIG. 7) verify that the observed inward flow can be explained by Marangoni convection. It is caused by temperature-induced differences in interfacial tension between water and oil. More precisely, local heating decreased the interfacial tension at the droplet's top and bottom, triggering Marangoni fluid flow along the interface. Due to the cylindrical symmetry, toroidal vortices arose in the upper and lower droplet hemisphere.

Figure 4:
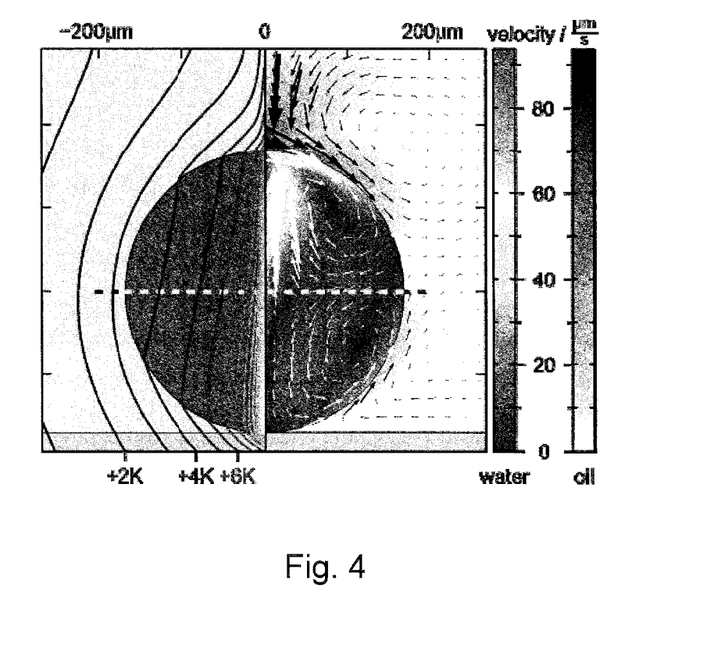
FIG. 4 is a numerical simulation of temperature and flow fields in a vertical cut through a 20 droplet after 0.2 s of heating.

In particular, FIG. 4 is a numerical simulation of temperature and flow fields in a vertical cut through a 20 droplet after 0.2 s of heating. Thus, FIG. 4 shows the tori's cross sections in a vertical cut. The dashed line indicates the central horizontal plane. Isotherms on the left side indicate the temperature increase induced by the focused IR laser. The right side of FIG. 4 shows the experimentally observed inward flow in the central horizontal plane comprises the boundary of two toroidal vortices. The vortices are driven by Marangoni convection at the water-oil interface and have already reached the steady state. The location of the vortex boundary only weakly depends on the oil layer thickness. Here, the flow is directed inward in the upper and lower vortex, which agrees with the experimental observation in this plane.

Figure 5:
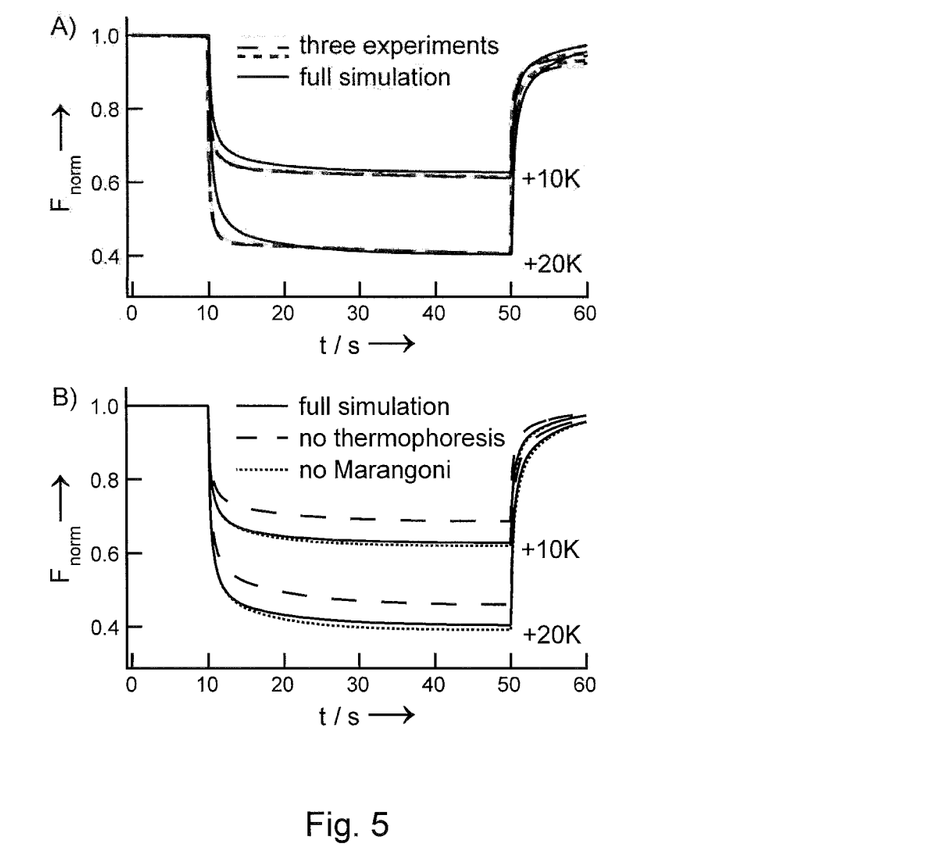
FIG. 5 shows the fluorescence time traces from locally heated 20 droplets in experiment and simulation.

FIG. 5 shows the fluorescence time traces from locally heated 20 droplets in experiment and simulation. Simulated traces were averaged over the droplet's central cylindrical volume (d=30 ram). After flow field analysis, fluorescence time traces, the basis for the binding measurements we recorded, in 20 nl-Alexa 647 samples (FIG. 5A). In particular, the FIG. 5 A) measurements of three Alexa 647-samples (grey, blue, red) overlap with minor deviations. This demonstrates the low batch-to-batch variation and the technique's high reproducibility. Moreover, experimental traces agree with simulated ones (black). Having turned on the heating laser (t=10 s), the fluorescence intensity Fnorm falls abruptly due to the dye's temperature dependence (0.1 s timescale). Thermophoretic molecule motion leads to slow depletion until thermophoresis and backdiffusion equilibrate within a few seconds. Subsequent slow warming of the entire sample slightly reduces the dye's intensity. When the heating is turned off (t=50 s), Fnorm recovers due to the dye response and isothermal backdiffusion. A larger ΔT enhances dye response and thermophoresis.

The experimental curves are highly reproducible and confirmed by the aforementioned simulations. A series of different events can be identified in agreement with standard capillary measurements. When the heating laser is turned on, the fluorescence intensity falls abruptly due to the dye's temperature dependence. Afterward, thermophoretic molecule motion leads to depletion resulting in a slow fluorescence decrease. Thermophoresis and backdiffusion equilibrate within a few seconds. Subsequent slow warming of the entire sample slightly reduces the dye's fluorescence intensity, but does not affect the measurement. When heating is turned off, fluorescence recovers due to the dye's response and backdiffusion. FIG. 5A shows larger ΔT enhances dye response and thermophoresis in experiment and simulation. To assess the contribution of Marangoni convection and thermophoresis to the fluorescence time traces, simulations excluding either effect were performed (FIG. 5B). FIG. 5 B) shows contributions to the decrease in Fnorm quantified via simulation. Omitting Marangoni convection led to a negligible change of 0.008 (dotted). When thermophoresis was disregarded, the signal changed by 0.06 (dashed).

Further implementation details are given below. When neglecting Marangoni convection, the flow fields differed considerably, but the fluorescence signal was only slightly altered. Upon removal of thermophoresis from the simulation, however, the time traces changed significantly. This demonstrates that thermophoresis prevailed against the convective flows.

Figure 6:
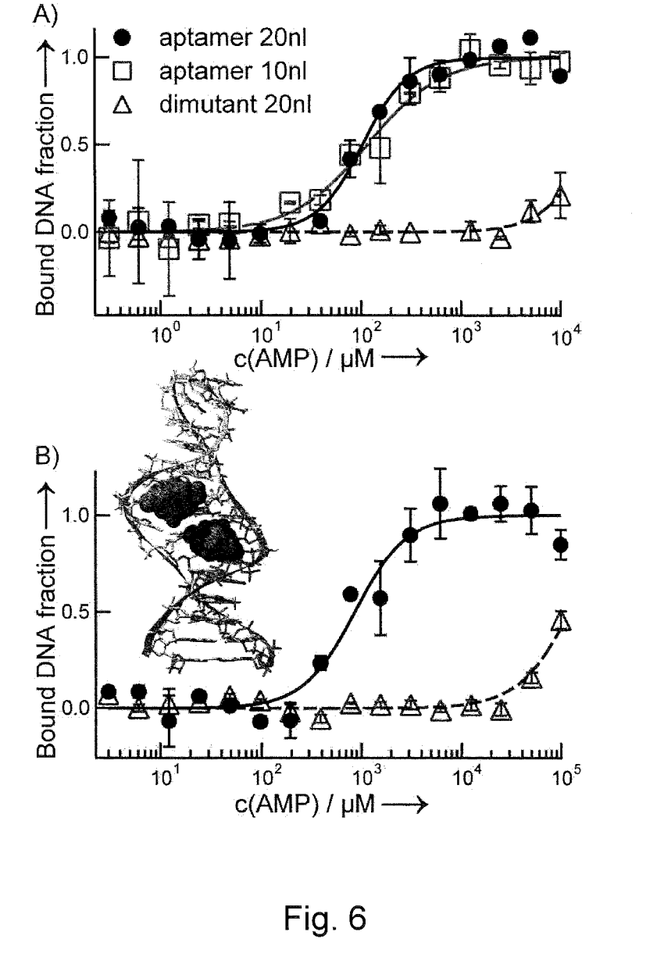
FIG. 6 shows that nanoliter thermophoresis quantifies AMP-aptamer binding.

FIG. 6 shows that nanoliter thermophoresis quantifies AMP-aptamer binding. Upon AMP-titration to labeled aptamer-DNA (c=2 μM), the dye's temperature response and thermophoretic mobility changes (ΔT=6 K). Mean values of measurements in at least two individual nl-samples were fit to the Hill equation; error bars represent the standard deviation. FIG. 6 A) shows a selection buffer. In 10 nl-samples, the fit revealed EC50=(11614) M and n=1.9±0.3 (red squares). In 20 nl-samples, EC50=(104±10) μM and n=1.2±0.1 were determined (black circles). These values are in good agreement with each other and literature. A dinucleotide mutant showed a 200-fold reduced EC50 of 20 mM (blue triangles). FIG. 6 B) shows PBS. In 20 nl-samples, EC50=(0.900.13) mM was found (black circles). This 10-fold affinity reduction in PBS compared to selection buffer confirms and quantifies the aptamer's buffer dependence. With n=1.6±0.4, the Hill coefficient was not significantly affected by the buffer. The mutant showed a 130-fold reduced affinity (EC50=0.12 M, blue triangles). The inset in FIG. 6 B) shows that determined Hill coefficients are consistent with the previously reported tertiary structure (NDB code 1AW4): an aptamer (grey) binds two AMP molecules (red).

Having characterized thermophoresis in droplets under oil, the inventors of the present invention evaluated its applicability for biomolecule interaction studies. A 25 mer DNA aptamer which binds adenosine and its phosphorylated analogues was analysed. This aptamer has previously been studied extensively. For nl-interaction studies, a constant concentration of fluorescently labeled aptamer (c=2 μM) was added to a serial dilution of adenosine 5' monophosphate (AMP). AMP and aptamer were mixed after the nl-transfer. As mentioned above, plates with funnel-shaped wells are preferred and were used to obtain the above mentioned results. Thus, mild centrifugation reliably coalesced individual AMP and aptamer portions. After coalescence, the concentration of AMP and aptamer equilibrated in the entire sample via diffusion. The short diffusion times through the small 10 nl- or 20 nl-samples guaranteed complete mixing within minutes. Diffusive mixing with manual premixing were compared, wherein both methods are considered to be substantially equally effective.

Figure 8:
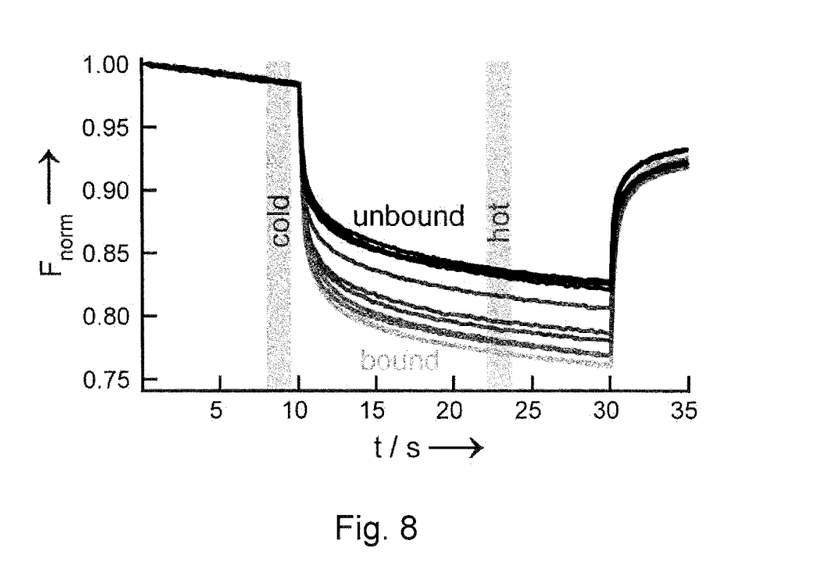
FIG. 8 shows raw fluorescence time traces of aptamer without and with different concentrations of AMP.

The mixed samples were locally heated. The resultant thermophoretic depletion of free aptamer significantly differed from its bound complex with AMP (FIG. 8). In addition, the temperature response of the aptamer's fluorophore changed upon AMP binding. The fluorescence after dye response and thermophoresis was divided by the fluorescence before heating as described in FIG. 8. Since this relative fluorescence can be approximated as linear to the bound aptamer fraction, it was directly fit to the Hill equation.

Using the original selection buffer according to Huizenga et al., it is found an EC50 of (116±14) M in 10 nl-samples (FIG. 6A). In 20 nl-samples, an EC50 of (104±10) μM was determined. Both values are in good agreement with each other and the literature value of (87±5) μM from capillary thermophoresis. The determined Hill coefficients of n=1.2±0.1 (10 nl) and n=1.9±0.3 (20 nl) indicate cooperative binding of more than one AMP, which is consistent with the previously reported tertiary structure of the complex (FIG. 5, inset). Moreover, the Hill coefficients only slightly deviate from each other and confirm the literature value (n=1.4). As a control, the inventors compared the AMP-affinity of the aptamer and of a DNA oligonucleotide with the same length but two point mutations. The dinucleotide mutant showed a 200-fold reduced EC50 of approximately 20 mM. This demonstrates the binding signal's specificity.

To quantify the AMP-aptamer's reported buffer dependence, binding was measured in PBS (FIG. 6B). An EC50 of (0.90±0.13) mM was found, corresponding to a 10-fold affinity reduction compared to selection buffer. This reduction is not surprising, as the aptamer has originally been evolved in and thus optimized for its selection buffer. A dominant effect can most likely be ascribed to magnesium ions: while the selection buffer contained 5 mM MgCl2, the inventors used PBS without Mg2+. Magnesium ions do not only stabilize DNA, but can also bind and neutralize AMP's phosphate group and, hence, reduce repulsion to phosphates in the aptamer-DNA's backbone. A reduction of the MgCl2-concentration from 5 to 0 mM has been reported to significantly reduce AMP-aptamer retention in affinity chromatography. This is in accordance with the EC50-differences that we found in nl-thermophoresis. The Hill coefficient was not significantly affected by the buffer, it was n=1.6-0.4 in PBS. The mutant control showed a 130-fold reduced EC50 of approximately 0.12 M compared to the aptamer.

The successful quantification of affinity, cooperativity, and buffer dependence evidences the presented method's applicability and reliability regarding aptamer analysis. This type of study is most likely to gain in importance, now that the comprehensive aptamer patent portfolio, which presumably has suppressed many commercial applications, is starting to expire. In addition, nl-thermophoresis is a highly attractive analysis tool for other biomolecules including peptides or proteins, and for complex bioliquids like blood. The suitability for these studies remains to be tested but— judging from the application depth of capillary thermophoresis—can be expected. Sample preparation is unlikely to be limiting, as the liquid handler can be deployed for various solution types. The inventors further produced stable droplets of 50% human blood serum (FIG. 1, inset) as required for thermophoretic diagnostics. Diffusive mixing after nl-transfer was successful. Hence, an assay design in which a stock dilution series of a biomolecule target is tested against a high number of binding partners seems very practical. It could also be combined with our previously published diagnostic autocompetition approach. A stock dilution of an unlabelled tracer for the biomarker of interest would then be tested against multiple patient sera, supplemented with a constant amount of labeled tracer.

Compared to conventional capillary thermophoresis, a 50-fold volume reduction was achieved. This leads to an enormous potential for high-throughput screens, even more so, as the easy-to-handle multi-well plates promote automation.

As a further advantage, the nl-transfer of the present invention is contact-free, which exempts from washing steps and minimizes cross contaminations, a prerequisite especially for diagnostic applications. After transfer, the sample is preferably not in direct contact with the well plate surface, but forms a surfactant surrounded droplet inside the oil. This can significantly reduce unspecific surface adhesion of biomolecules ("sticking"), an often encountered challenge in capillary thermophoresis. The potential elimination of sticking represents a preferred benefit, even if surfactant and oil might have to be adapted for different sample types.

Considering these advantages, the achieved miniaturization, and the extensive characterization in experiment and simulation, droplet thermophoresis promises diverse applications in various fields of the life sciences.

Experimental Section

In the following, further details on the experimental setup, which was used to show practicability of the present invention, will be given. It is, however, explicitely pointed out that the following setup merely refers to a possible preferred embodiment which should not limit the present invention. Firstly, nanoliter samples were prepared on an Echo 550 liquid handler (Labcyte Inc, USA). Echo qualified 384-well low dead volume source plates (Labcyte Inc) were filled manually. Air bubbles were preferably avoided via reverse pipetting and centrifugation (2 min, 1000×g) of the source plate. Destination plates (1536-well imp@ct plates, flat bottom; Greiner Bio-One GmbH, Germany) were manually filled with 0.5 l/well microbiology mineral oil (Carl Roth GmbH, Germany) with 4.5% (v/v) Span 80, 0.5% (v/v) Tween 80 (Sigma Aldrich Chemie GmbH, Germany). To remove air bubbles, destination plates were centrifuged (2 min, 1000×g). Taking into account oil properties and destination well dimensions, the oil layer was chosen to be thin enough to prevent dripping from the upside-down plate during transfer, but also thick enough to fully incorporate droplets with diameters of approximately 270 or 340 μm (10 or 20 nl). Due to deflection by the oil, droplets tended to not reach the well floor. To sink the droplets, plates were shortly centrifuged (one pulse up to ≤500×g). Typically, two or more individually transferred nl-portions had to be coalesced, which required 5-10 min of centrifugation. To avoid droplet damage, 500×g should not be exceeded.

The nl-thermophoresis setup was built from optomechanical components ordered from Thorlabs GmbH, Germany. A red LED (625 nm, 1600 mA) with an aspheric condenser lens (Thorlabs GmbH) was used for fluorescence excitation. An Ag-coated mirror (AHF Analysentechnik AG, Germany), an infinity-corrected tube lens (Thorlabs GmbH) and a CCD-camera (Stingray F-145B; Allied Vision Technologies GmbH, Germany) were employed for imaging. Cy5-fluorescence filters were ordered from Laser Components GmbH, Germany. Temperature gradients were created with an infrared laser diode (l=1480 nm, P<500 mW; Fibotec Fiberoptics GmbH, Germany) coupled into the fluorescence light path with a heat-reflecting mirror (NanoTemper Technologies GmbH, Germany) and focused into the fluid with a 20× plan-apochromat objective (NA=0.8; Carl Zeiss AG, Germany). The optical components were mounted onto three orthogonal precision translation stages (Physik Instrumente GmbH, Germany; Edmund Optics Inc., USA).

All measurements were performed at room temperature. The temperature increase was measured utilizing the temperature dependence of the fluorescent dye Alexa 647 (Life Technologies). Flows were visualized with 0.05% (m/v) crimson fluorescent microspheres (d=1.0 μm; Life Technologies, USA) in MilliQ water with 3.25 μM Alexa 647.

Binding assays were performed in selection buffer (20 mM Tris-Cl, 300 mM NaCl, 5 mM MgCl2, pH 7.6) and in PBS (10 mM Na2HPO4, 1 mM KH2PO4, 137 mM NaCl, 2.7 mM KCl, pH 7.0). AMP sodium salt (Sigma Aldrich Chemie GmbH) was diluted starting at maximum final concentrations of 10 mM (selection buffer) or 0.1 M (PBS). DNA oligonucleotides (biomers.net GmbH, Germany) with the sequences 5'-Cy5-CCT GGG GGA GTA TTG CGG AGG AAG G-3 (aptamer) or 5'-Cy5-CCT tGG GGA GTA TTG CGG AtG AAG G-3' (mutant) were added to the AMP-dilution steps manually prior to (PBS) or during droplet transfer (selection buffer) to yield final oligonucleotide concentrations of 2 μM and final droplet volumes of 10 or 20 nl. Fluorescence after thermophoresis was averaged over a (30×30) μm area in the heat spot and normalized to the cold fluorescence. Mean Fnorm-values of at least two nl-samples from identical stocks were fit to the Hill equation. Error bars represent the standard deviation.

Finite element simulations were done using COMSOL Multiphysics (COMSOL Inc., USA). Flows in the aqueous droplet and the oil were described by cylindrically symmetric incompressible Navier-Stokes equations, combined with equations for thermal convection and conduction, laser absorption, and Marangoni convection at the interface. Molecules inside the droplet are subject to diffusion, convection and thermophoresis. The temperature dependence of the interfacial tension was adjusted to reproduce experimentally measured flow velocities. For the time traces in FIG. 4b, the fluorescence was averaged over a cylindrical volume (d=30 μm) in the droplet center.

Numerical Simulation of Locally Heated Droplets Excluding Marangoni Convection or Thermophoresis The physics in the aqueous droplet are described by a set of coupled partial differential equations. In addition to the incompressible Navier-Stokes equations, equations for thermal convection and conduction, and laser absorption, two more equations are required. For Marangoni convection, this is $$\eta^{(i)}\left[rn \cdot \nabla\left(\frac{t \cdot v}{r}\right)\right] = \gamma_T t \cdot \nabla T,$$

which must hold at the oil-water interface. [1]n and t are the normal and tangential unit vectors, v is the fluid velocity and r the radial coordinate. $\gamma_T = \partial\gamma/\partial T$ denotes the temperature dependence of the interfacial tension, $\eta^{(i)}$ the viscosity of water or oil on each side of the interface.

The distribution of the solute inside the droplet is described by a convection-diffusion equation, extended by a term for thermophoresis:

$$\frac{\partial c}{\partial t} + \nabla[(-D\nabla - D_T \nabla T + v)c] = 0.$$

D is the diffusion coefficient and $D_T$ the thermodiffusion coefficient. Their ratio is the Soret coefficient $S_T = D_T/D$.

To quantify the respective contributions of Marangoni convection and thermophoresis to the observed fluorescence decrease, two control simulations were performed. In these controls, either the Soret coefficient $S_T$ or the temperature dependence of the interfacial tension $\gamma_T$ has been set to zero.

In the latter case ($\gamma_T = 0$, "no Marangoni"), the flow fields in the droplet are very different from those in the full simulation. However, the fluorescence time traces are not altered significantly. On the other hand, setting $D_T = 0$ (hence $S_T = 0$, "no thermophoresis") strongly reduces the magnitude of the fluorescence decrease. Therefore, the Soret coefficient of the solute strongly affects the observed fluorescence time traces. Moreover, this signal is not masked by the convective flows.

Influences from Droplet Size

Figure 7:
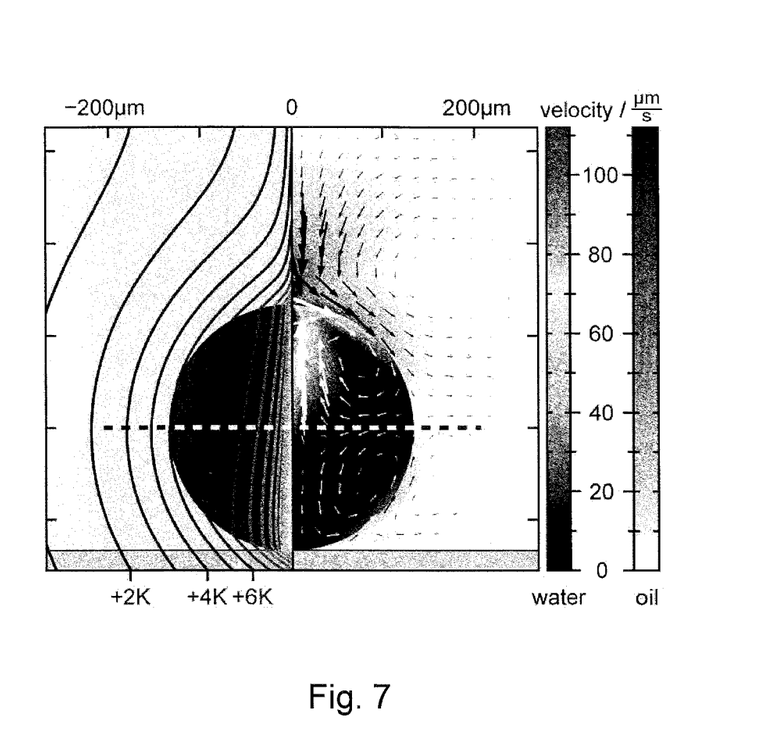
FIG. 7 shows a numerical simulation of temperature and flow fields in a vertical cut through a 10 droplet after 0.2 s of heating which is similar to FIG. 3.

To assess the influence of the droplet size on the thermophoresis measurements, droplets of two different sizes, 20 nl (340 μm) and 10 nl (270 μm) were simulated (FIG. 4 and FIG. 7). The resulting flow fields and temperature distributions were highly similar. The mean flow velocity was 12 m/s in the 20 droplet and 14 μm/s in the 10 nl droplet. The average temperature increase in the measurement volume (d=30 μm) was 10 K in the 20 droplet and 11.5 K in the 10 droplet (for the same heating power). These minor differences illustrate that the measurement principle is independent of the droplet size in the relevant range. Therefore, small deviations from the target volumes will not have any considerable effect on the thermophoresis measurements. The differences could even be fully avoided by decreasing the heating power in 10 nl FIG. 7 shows the numerical simulation of temperature and flow fields in a vertical cut through a 10 droplet after 0.2 s of heating. This figure is completely analogous to FIG. 3. In particular, the laser power is the same as for the 20 nl droplet.

The accuracy of the Labcyte ECHO 550 liquid handler for aqueous buffers was previously analyzed by Harris et al. In this systematic analysis, deviations from the expected volume lay below 2% for PBS or TRIS buffer with MgCl2 for all tested volumes. This high accuracy is achieved, as the liquid handler measures fluid height and properties before transfer and then calibrates automatically.

The transfer volume deviations of <2% does not affect the nl-thermophoresis measurements, as experiments in both, 20 nl and 10 nl droplets gave consistent results. This corresponds to a volume difference of 50%. In addition, simulations in 20 nl and 10° nl were almost identical in terms of convective flows, temperature distribution, and fluorescence time traces (FIG. 3 B) with FIG. 7).

Volume deviations correspond to concentration errors, when mixing two compounds for binding studies. However, a concentration error <2% is very small compared to e.g. manual pipetting of small pl-volumes.

Taken together, the inaccuracy of the transfer is so small, that it is not critical for our technique. Furthermore, rare outliers in droplet size e.g. due to inaccurate source well filling or oil layer preparation can easily be identified with the optical measurement setup.

FIG. 8 shows fluorescence time traces of labeled aptamer with and without AMP during a thermophoresis experiment in 20 nl-selection buffer droplets. The heating laser was turned on after 10 s, which led to a fluorescence decrease because of two events. Firstly, the intensity of the fluorophore decreased due to the temperature increase. Secondly, thermophoretic molecule movement away from the heat spot led to depletion and thus lowered the fluorescence. Both events were influenced, when AMP bound to the aptamer. The temperature response of the fluorophore is sensitive to its local environment. This temperature response is thus influenced by binding in close proximity to the dye or by conformational changes of the aptamer during the binding event. In case of the AMP-aptamer binding, the dye's temperature response was smaller for the unbound aptamer than for the bound complex. Thermophoresis is highly sensitive to binding induced changes of various molecular properties. The thermophoretic depletion was weaker for free aptamer than for its complex with AMP.

Titration of AMP two a constant aptamer amount changed the ratio of bound and unbound aptamer. Thus, the titration steps showed a stepwise change in the dye's temperature response and the thermophoretic depletion.

Thus, FIG. 8 shows raw fluorescence time traces of aptamer without and with different concentrations of AMP (20 nl, selection buffer). Unbound aptamer (top, black) shows a smaller temperature response of its fluorophore and a weaker thermophoretic depletion than the bound complex with AMP (bottom, orange). To quantify binding, AMP was titrated against a constant aptamer concentration. This led to a changing ratio of unbound and bound aptamer and thus to a stepwise change of the time traces (middle, brown). The fluorescence after dye response and thermophoresis (hot, red) was divided by the fluorescence before heating (cold, blue). This relative fluorescence was analyzed further (see below).

FIG. 8 illustrates the first analysis step of the fluorescence time traces: The thermophoresis before heating (cold, blue) was averaged between 8.4 s and 9.5 s, and the fluorescence after heating (hot, red) between 22.4 s and 23.5 s. Afterward, the hot fluorescence was divided by the cold fluorescence, to yield the strength of dye temperature response and thermophoretic depletion. This signal can be approximated as linear to the bound aptamer fraction. It can thus directly be fit to the binding model. As AMP and aptamer have been reported to show cooperative binding, we fit the data to the Hill equation. The Hill equation revealed the EC50 and the Hill coefficient.

To obtain the bound fraction, the inventors subtracted Fhot/Fcold of the unbound aptamer as a baseline and normalized the curve to a fully bound plateau of 100%. Finally, the bound fraction was plotted on a linear y-axis against the AMP concentration on a log 10 x-axis (see FIG. 6).

The invention claimed is:

1. A method for thermo-optical measurements in a first volume of aqueous solution comprising particles of interest, the method comprising:
   providing the first volume of aqueous solution with a volume of less than 200 nl, wherein the aqueous solution is a first liquid and at least a part of the particles of interest are fluorescent particles;
   embedding the first volume of aqueous solution at least partly in a second liquid, wherein the second liquid does not absorb IR radiation, and wherein the aqueous solution is stabilized within the second liquid by means of a surfactant;
   irradiating a laser light beam into the first volume to obtain a spatial temperature distribution in the first volume around the irradiated laser light beam;

exciting fluorescently said fluorescent particles and detecting the fluorescence at least at one position or around one position in the first volume or detecting the fluorescence distribution of said fluorescently excited particles, wherein said detection of fluorescence is performed at least once at a predetermined time after the start of the laser irradiation; and determining a characteristic of the particles of interest from the detected fluorescence intensity or fluorescence intensity distribution; and wherein the first volume is formed by:
providing a destination plate with the second liquid;
providing a liquid sample of the aqueous solution containing said fluorescent particles
and generating at least one transfer droplet from said liquid sample; and
transferring at least one of said transfer droplets to the second liquid such that the first volume is formed by one or a plurality of said transfer droplets on the destination plate, wherein said first volume is at least partly embedded in said second liquid.

2. The method according to claim 1, wherein
a. the second liquid only partly embeds the first volume, such that the first volume is covered with a layer of the second liquid; or
b. the first volume is fully embedded within the second liquid; and/or
c. the aqueous solution is immiscible with the second liquid such that a boundary surface is formed between the aqueous solution and the second liquid.

3. The method according to claim 1, wherein the second liquid is non-aqueous, an oil, a surfactant, a surfactant-oil mix or a detergent-oil mix, which ensures that the aqueous solution of the first volume forms a droplet.

4. The method of claim 3, wherein the droplet is formed as one of a spherical, substantially spherical, egg shaped, oval, elongated, partly flat, partly convex or partly concave droplet, which comprises a substantially constant diameter.

5. The method according to claim 1, wherein
a. the destination plate is a multiwell plate and the second liquid is provided in at least one of the wells of the multiwell plate; and/or
b. the liquid sample is provided in a multiwell source plate.

6. The method according to claim 5, wherein the destination multiwell plate comprises conical wells and the first volume preferably touches a bottom of the conical well, wherein the multiwell plate is one of a 6, 12, 24, 48, 96, 384 or a 1536 multiwell plate.

7. The method according to claim 1, wherein the transfer droplets are generated by a droplet generator which comprises a transducer located below the multiwell source plate, wherein the transducer emits pulses to generate and transfer the transfer droplet from the multiwell source plate to the destination plate.

8. The method according to claim 7, wherein the transducer pulses are acoustic pulses.

9. The method according to claim 1, wherein the second liquid is admixed with the aqueous solution such that the first volumes of the aqueous solution are formed within the second liquid, wherein
said second liquid with said droplets is guided into a channel of capillary, such that the droplet is embedded within said channel or capillary, wherein said channel is a channel of a microfluidic device.

10. The method according to claim 9, wherein the droplets of the first liquid are provided in the second liquid as an emulsion.

11. The method according to claim 1, wherein the first volume is a droplet which is generated by means of a piezo based droplet generator.

12. The method according to claim 1, wherein
the volume of the first volume is smaller than 100 nl; and/or
the volume of the first volume is larger than 10 pl; and/or
the diameter of the bordered volumes is smaller than 200 µm; and/or
the diameter of the bordered volumes is larger than 500 nm.

13. The method according to claim 1, wherein the thickness of the second liquid is below 500 µm and so formed that and the oil film is centrifuged to create the oil film without bubbles, and centrifuged in a range between 1 to 1000 g.

14. The method according to claim 1, wherein the fluorescence is detected at least at any two positions or at around two positions in the first volume.

15. The method according to claim 1, wherein additionally the detection of fluorescence is performed at least once before the start of the laser irradiation.

16. The method according to claim 1, wherein laser is a IR laser and/or fluorescence is excited with a light emitting diode, LED (31), wherein the laser is a low power laser within the range of from 5 mW to 60 mW.

17. The method of claim 1, wherein the method is performed by a device for thermo-optical measurements in a first volume of aqueous solution, the device comprising:
a means for providing a first volume of the first liquid which is an aqueous solution, said first volume having a volume of less than 200 nl, wherein said first volume of aqueous solution is at least partly embedded in a second liquid;
a laser for irradiating a laser light beam into the first volume to obtain a spatial temperature distribution in the first volume around the irradiated laser light beam;
means for fluorescently exciting fluorescent particles in the first volume; and
means for detecting fluorescence and/or fluorescence distribution of the fluorescently excited particles.

18. The method of claim 17, wherein creating a droplet of an aqueous solution with a volume of less than 200 nl is performed by a device for creating the first volume, the device for creating the first volume comprising:
means for providing a liquid sample of aqueous solution; and
a transducer for transferring at least a transfer droplet from the liquid sample to the means for providing the first volume such that the first volume is at least partly embedded within the second liquid.

19. The method of claim 18, wherein providing the first volume is performed with a destination plate comprising a multiwell plate or a microfluidic device with at least a channel or capillary for obtaining said first volume at least partly embedded within the second liquid.

20. The method according to claim 1, wherein transferring further comprises guiding the droplet using an electric field.

* * * * *